US011806007B2

(12) United States Patent
Börner et al.

(10) Patent No.: US 11,806,007 B2
(45) Date of Patent: Nov. 7, 2023

(54) SUTURING DEVICE

(71) Applicant: Suturion AB, Ramlösa (SE)

(72) Inventors: Gabriel Börner, Ramlösa (SE); Mats Christensson, Staffanstorp (SE); Rickard Norenstam, Löddeköpinge (SE)

(73) Assignee: Suturion AB, Ramlösa (SE)

( * ) Notice: Subject to any disclaimer, the term of this patent is extended or adjusted under 35 U.S.C. 154(b) by 257 days.

(21) Appl. No.: 17/057,000

(22) PCT Filed: May 23, 2019

(86) PCT No.: PCT/EP2019/063309
§ 371 (c)(1),
(2) Date: Nov. 19, 2020

(87) PCT Pub. No.: WO2019/224296
PCT Pub. Date: Nov. 28, 2019

(65) Prior Publication Data
US 2021/0196262 A1    Jul. 1, 2021

(30) Foreign Application Priority Data

May 25, 2018  (SE) .................................... 1850630-3

(51) Int. Cl.
*A61B 17/062* (2006.01)
*A61B 17/06* (2006.01)

(52) U.S. Cl.
CPC .. *A61B 17/0625* (2013.01); *A61B 2017/0609* (2013.01); *A61B 2017/06019* (2013.01); *A61B 2017/06047* (2013.01)

(58) Field of Classification Search
CPC ...... A61B 17/0625; A61B 2017/06019; A61B 2017/06047; A61B 2017/0609; A61B 17/0491
See application file for complete search history.

(56) References Cited

U.S. PATENT DOCUMENTS 5,571,090 A    11/1996  Sherts
5,674,229 A    10/1997  Tovey et al.
(Continued)

FOREIGN PATENT DOCUMENTS

CA    3005638 A1    5/2017
EP    0764426 A2    3/1997
(Continued)

*Primary Examiner* — Tan-Uyen T Ho
*Assistant Examiner* — David P Stein
(74) *Attorney, Agent, or Firm* — DINSMORE & SHOHL LLP

(57) ABSTRACT

A suturing device with built-in needle-transfer of a double-ended needle has a first jaw element with a first needle lock device for retaining and releasing a first end of the needle; a second jaw element with a second needle lock device, wherein the jaw elements are movable between an open and closed position; and a needle-transferring mechanism for alternately transferring the needle from one of the jaw elements to the other when the jaws are moved from the open to the closed position. The needle-transferring mechanism includes a first rotatable wheel connected to the first needle lock device, the first wheel having a first wheel inner portion rigidly connected to a first wheel outer portion and a second rotatable wheel connected to the second needle lock device, said second rotatable wheel comprising a second wheel inner portion rigidly connected to a second wheel outer portion.

20 Claims, 11 Drawing Sheets

(56) References Cited

U.S. PATENT DOCUMENTS

| | | | |
|---|---|---|---|
| 5,674,230 | A | 10/1997 | Tovey et al. |
| 5,728,113 | A | 3/1998 | Sherts |
| 5,814,054 | A | 9/1998 | Kortenbach et al. |
| 9,901,336 | B2 | 2/2018 | Hashimoto |
| 2009/0312773 | A1 | 12/2009 | Cabrera et al. |
| 2013/0304096 | A1 | 11/2013 | Nguyen et al. |
| 2014/0257345 | A1* | 9/2014 | Holwerda .......... A61B 17/0625 606/145 |
| 2014/0276988 | A1 | 9/2014 | Tagge et al. |
| 2016/0199058 | A1 | 7/2016 | Chlysta |
| 2016/0367239 | A1 | 12/2016 | Mumaw et al. |
| 2017/0071597 | A1 | 3/2017 | Gorski et al. |
| 2017/0340320 | A1 | 11/2017 | Baril |
| 2019/0083086 | A1* | 3/2019 | Klaffenböck .......... A61B 17/06 |

FOREIGN PATENT DOCUMENTS

| | | |
|---|---|---|
| FR | 337579 A | 4/1904 |
| WO | 9811829 A1 | 3/1998 |
| WO | 2008045333 A2 | 4/2008 |
| WO | 2008045353 A2 | 4/2008 |
| WO | 2013032329 A1 | 3/2013 |
| WO | 2014030544 A1 | 2/2014 |
| WO | 2015109159 A1 | 7/2015 |
| WO | 2017007316 A1 | 1/2017 |
| WO | 2017155406 A1 | 9/2017 |

\* cited by examiner

SUTURING DEVICE

CROSS-REFERENCE TO RELATED APPLICATIONS

This application is the U.S. national stage of PCT/EP2019/063309 filed May 23, 2019, which claims priority of Sweden patent application 1850630-3 filed May 25, 2018, both of which are hereby incorporated by reference in their entirety.

FIELD OF THE INVENTION

The present disclosure relates to an improved suturing device, in particular to an automated or semi-automated disposable suturing device. Preferably, the device is a one-handed suturing device.

BACKGROUND OF INVENTION

Surgical procedures in the abdominal cavity requires access that can be achieved via open surgery or minimally invasive techniques. Open surgical procedures are very common and about 2 million procedures are performed annually in the US. Following the procedure the abdominal wall has to be closed. Experimental and clinical data gives sound information about the surgical technique required to minimize abdominal wall complications after surgery. Wound infections and incisional hernias are reduced if a continuous suture technique is used and the thread is four times the length of the incision. The stiches should be small and placed tightly. The suturing process is tedious and time-consuming and difficult to achieve following long and strenuous surgical procedures. Operating room time is expensive and time savings can provide care for more patients. Furthermore, abdominal closure is the most common ground for needle injuries during surgery.

The existing suturing instruments are associated with a number of disadvantages and inconveniences. They are typically difficult to use, do not guarantee the safety of the patient, lack precision and are often mechanically complex. It would therefore be desirable to provide an instrument that would help the surgeon to adhere to the correct way of closing the abdomen and to reduce the time needed to perform the suturing. Preferably, such an instrument should also reduce the risk for prick injuries, simplify suture placement and be mechanically simple and robust.

SUMMARY OF INVENTION

The present disclosure relates to an improved suturing device with built-in needle-transfer of a double-ended needle. The suturing device may be a one-handed device, wherein the transfer of the needle between the jaws preferably is automatic in the sense that the mechanism for opening/closing of the jaws also controls, or is mechanically synchronized with, the transfer of the needle, preferably without the need of additional switches for controlling the transfer of the needle.

In a first embodiment the suturing device comprises:
  a first jaw element comprising a first needle lock device for retaining and releasing a first end of the double-ended needle;
  a second jaw element comprising a second needle lock device for retaining and releasing a second end of the double-ended needle,
   wherein the first and second jaw elements are movable in relation to each other between an open position and a closed position;
  a needle-transferring mechanism for alternately transferring the double-ended needle from one of the jaw elements to the other when the first and second jaws are moved from the open position to the closed position, said needle-transferring mechanism comprising:
    a first rotatable wheel connected to the first needle lock device, said first rotatable wheel comprising a first wheel inner portion rigidly connected to a first wheel outer portion; and
    a second rotatable wheel connected to the second needle lock device said second rotatable wheel comprising a second wheel inner portion rigidly connected to a second wheel outer portion,
  wherein a first force is propagated from the first jaw element to the second rotatable wheel and wherein a second force is propagated from the second jaw element to the first rotatable wheel when the first and second jaw elements are moved in relation to each other from the open position to the closed position, thereby causing the first and second rotatable wheels to rotate, wherein the first and second rotatable wheels are arranged such that a rotation of the first and second rotatable wheels causes one of the needle lock devices to lock the double-ended needle and the other needle lock device to release the double-ended needle. The needle-transferring mechanism may thereby be arranged such that a difference in rotation and/or a difference in a rotation cycle, for example a shift/offset, between the first and second rotatable wheels provide the transfer mechanism.

The presently disclosed suturing device with built-in needle-transfer provides an accurate and robust design of a suturing device for improved, in particular faster and more precise, surgical suturing, wherein a user may push the jaws together repeatedly using one hand to transfer the doubled-ended needle back and forth between the jaws. The process of releasing the needle from one jaw and locking the needle in the other jaw when the jaws are closed may be effectuated by a sequential mechanism inside the tool. In a first embodiment, two wheels turn in opposite directions when the jaws are closed, which allows opening and closing of needle retention elements alternately, such that the needle is passed back and forth between the first and second jaw when the jaws are opened and closed repeatedly. In a second and alternative embodiment, the two wheels may instead be arranged to rotate in the same direction. However, if each wheel has an outer profile which engages with the needle lock devices and controls the position of the needle lock elements in the axial direction of the corresponding jaw, a shift in the outer profiles between the wheels may provide the mechanism for alternately transferring the double-ended needle from one of the jaw elements to the other when the first and second jaws are moved from the open position to the closed position.

Preferably, the needle-transferring mechanism is arranged to operate in a coordinated sequence of steps triggered by the angle between the jaws, which changes during a closing process. Two wheel drive mechanisms, for example in the form of drive shafts, may engage with both the jaws and the wheels in such a way the wheels start turning when the angle between the jaws are lower than a threshold angle during a closing process. Below this threshold, when the wheels start turning as the jaws are being closed, the outer profile of the wheels may define further steps, wherein each step may correspond to a configuration of the first and second needle lock devices. In one embodiment, each needle lock device comprises a wheel engagement element which moves backwards/forwards in the axial direction of the jaws to retain/release the needle when the wheels rotate. This mechanism is further explained in examples in the detailed description of the invention below.

The two wheels may be shaped such that the process is the same when the needle is passed form the first jaw to the second jaw compared to when the needle is passed from the second jaw to the first jaw. This allows the user to operate the suturing device by pushing the two jaws together, whereby the needle is transferred from a first jaw to a second jaw, then relying on the force of a jaw opening spring to open the jaws, then pushing the jaws together again to transfer the needle from the second jaw to the first jaw, and so forth. The needle-transferring mechanism may thereby be automatic in the sense that there are no additional switches for controlling the transfer of the needle.

DETAILED DESCRIPTION OF THE INVENTION

Figure 1:
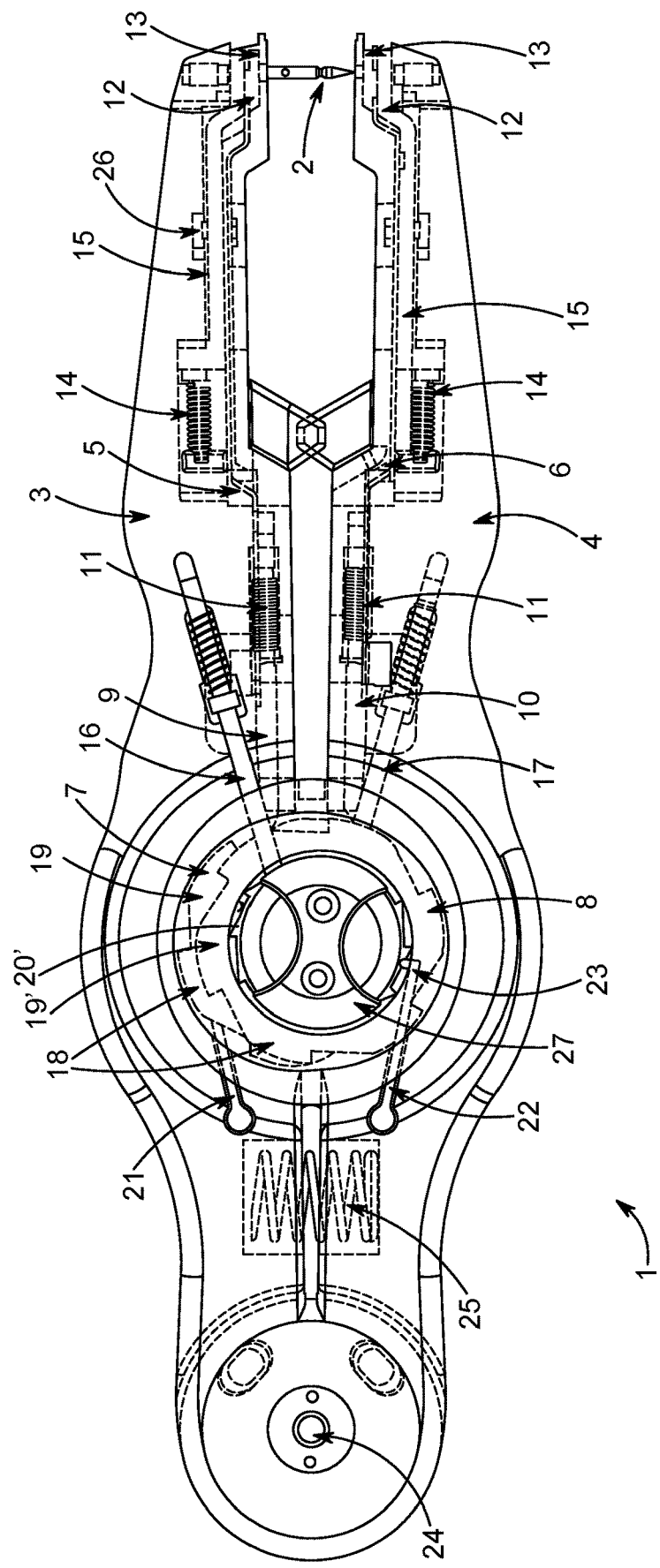
FIG. 1 is a view of an embodiment of the presently disclosed suturing device with built-in needle-transfer of a double-ended needle, wherein two rotatable wheels are arranged to rotate in opposite directions to control the retention and release of two needle lock devices.

The present disclosure relates to a suturing device with a needle-transfer of a double-ended needle, the suturing device comprising: a first jaw element comprising a first needle lock device for retaining and releasing a first end of the double-ended needle; a second jaw element comprising a second needle lock device for retaining and releasing a second end of the double-ended needle, wherein the first and second jaw elements are movable in relation to each other between an open position and a closed position; and a needle-transferring mechanism for alternately transferring the double-ended needle from one of the jaw elements to the other when the first and second jaws are moved from the open position to the closed position. More precisely the double-ended is alternately transferred from one needle lock device to the other needle lock device. The suturing device may be a suturing device for closing the abdomen. Typically, the jaw elements are pivotable in relation to each other around a common pivot joint. Preferably, the needle-transferring mechanism comprises: a first rotatable wheel connected to the first needle lock device; and a second rotatable wheel connected to the second needle lock device. The first and second rotatable wheels may be arranged such that a rotation, such that a difference in rotation and/or a shift or offset, between the first and second rotatable wheels causes one of the needle lock devices to lock the double-ended needle and the other needle lock device to release the double-ended needle when the first and second jaw elements are moved in relation to each other from the open position to the closed position. In one embodiment, the first and second rotatable wheels are arranged to rotate simultaneously and/or synchronized, preferably with the same rotational speed in order to provide a synchronized and/or coordinated release and retention of the two needle lock devices. The rotatable wheel based solution allows the user to transfer the needle form one jaw to the other in one movement, for example by pushing the jaws together directly or by pushing two handles together, thereby pushing the jaws together. If the user then releases the jaws or handles, a spring coil, or another solution providing the same functionality may force the jaws to return to an open position. This mechanism may be provided by means of a jaw opening spring arranged between the first jaw element and the second jaw element. If the user then pushes the jaws together again, the needle-transferring mechanism may cause the double-ended needle to transfer back from the second jaw to the first jaw. This means that the user can repeatedly push the jaws together and then let the spring coil move them back to the open position to perform a suturing process.

In particular this automatic or semi-automatic mechanism may allow for one-handed use. The device is robust, efficient and relatively simple in its construction. The mechanism is hence suitable for a disposable suturing device.

A first embodiment of the presently disclosed suturing device comprises two rotatable wheels, wherein the first and second rotatable wheels are arranged to rotate in opposite directions when the first and second jaw elements are moved in relation to each other from the open position to the closed position, thereby causing one of the needle lock devices to lock the double-ended needle and the other needle lock device to release the double-ended needle. The rotation of two rotatable wheels may be driven by shafts connected to the jaw elements. When the jaw elements are closed towards each other, the shafts may push the wheels to rotation. Outer profiles of the wheels may thereby cause the needle lock devices to lock and release the double-ended needle alternately.

A second embodiment of the presently disclosed suturing device comprises two rotatable wheels, wherein the first and second rotatable wheels are arranged to rotate in the same direction, and wherein outer profiles of the wheels are shifted in relation to each other when the wheel rotates. In this embodiment the shifted profiles may be arranged such that they control the needle lock devices to lock and release the double-ended needle alternately.

Needle Lock Device Mechanisms

A first needle lock device is associated with the first jaw element and a second needle lock device is associated with the second jaw element. A needle lock device within the present disclosure may be referred to as a complete mechanism for retaining and releasing one end of a double-ended needle. The needle lock device may thereby comprise a number of connected or engaging elements. A needle lock device may be incorporated into a jaw element. A needle lock device may engage or connect to one of the rotatable wheels in one end, and extend via, preferably inside, the jaw element, whereas the other end may be able to retain and release one end of the needle as explained in further detail below. Preferably, the first rotatable wheel engages with the first needle lock device and the second rotatable wheel engages with the second needle lock device. This can be achieved by wheel engagement elements engaging with the first and second rotatable wheels, respectively. As the wheel rotate, the outer profile of the wheels may move the wheel engagement elements backwards and forwards in the axial direction of the corresponding jaw element in response to a rotation of the corresponding rotatable wheel. Forwards has the meaning in the direction towards the free end of a jaw element. Consequently, backwards means the opposite direction, i.e. towards the wheels.

The wheel engagement elements may be engagement shafts. In order to maintain contact between the wheel engagement elements and the varying outer profiles of the rotatable wheels, each wheel engagement element may comprise a first spring coil configured to maintain a pressure from the wheel engagement element to the corresponding rotatable wheel.

As a person skilled in the art would understand, there are different solutions for controlling the retention and release of the double-ended needle based on the movement of the wheel engagement elements back and forth in the axial direction of each jaw element. FIG. 1 shows one embodiment in which each wheel engagement element is connected to a needle retention element extending in the longitudinal direction of the corresponding jaw element. Each needle retention element may comprise an opening, preferably adjacent to the freed ends of the jaw elements, where the suturing typically takes place, for receiving the double-ended needle. The opening may have a shape capable of locking the double-ended needle. One mechanical solution for locking the needle comprises an opening having a wide section and narrow section, for example a substantially key hole shaped opening. The double-ended needle may accordingly have a portion which is narrower or thinner than the rest of the needle, which, when introduced into the narrow section, such as a grove or slot, of the opening of the retention element, prevents the needle from movement in the longitudinal direction of the needle. The double-ended needle may have such a groove or slot in both ends.

Figure 6:
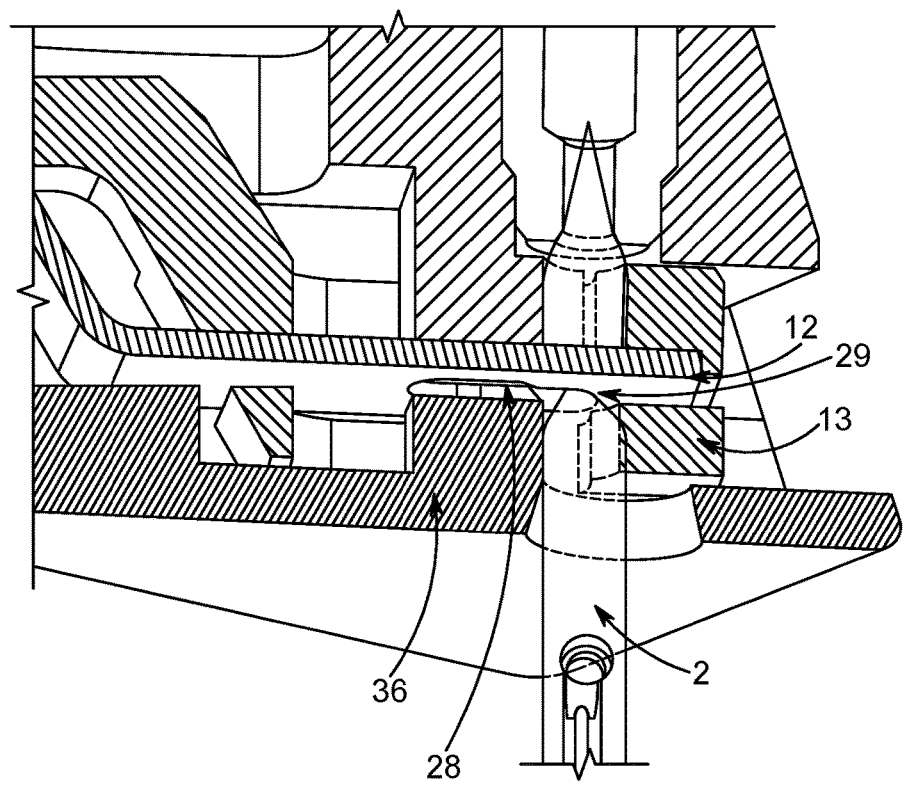
FIG. 6 is a detailed view showing an embodiment of the needle retention element with an opening for receiving and locking the needle and a needle pusher element.

In order to prevent that the needle, when locked in the narrow section of the opening, moves to the wide section and falls off, each needle lock device may comprise a needle pusher element configured to push the double-ended needle against a body part as shown in FIG. 6. The needle pusher element may be arranged to push the double-ended needle backwards towards a body part of the corresponding jaw element. A needle pusher connecting element may form part of the needle lock device and connect the wheel engagement element and the needle retention element. There may be a second spring configured to maintain a pressure on the needle pusher element towards the body part.

In addition to the built-in mechanism for retaining and releasing the needle the presently disclosed suturing device may comprise a manual needle release mechanism for manually releasing the needle from the jaw if needed. Each jaw may have its own manual needle release element. The manual needle release mechanism may be implemented as for example a pin, grip or button on the jaw, extending into the jaw and controlling for example the needle lock device or an element of the needle lock device, such as the retention element or the wheel engagement element.

Arrangements of Rotatable Wheels

As stated above, the needle-transferring mechanism comprises: a first rotatable wheel connected to the first needle lock device; and a second rotatable wheel connected to the second needle lock device. The first and second rotatable wheels may be arranged such that a difference in rotation between the first and second rotatable wheels causes one of the needle lock devices to lock the double-ended needle and the other needle lock device to release the double-ended needle when the first and second jaw elements are moved in relation to each other from the open position to the closed position.

A first embodiment of the presently disclosed suturing device comprises two rotatable wheels, wherein the first and second rotatable wheels are arranged to rotate in opposite directions when the first and second jaw elements are moved in relation to each other from the open position to the closed position, thereby causing one of the needle lock devices to lock the double-ended needle and the other needle lock device to release the double-ended needle. A second embodiment of the presently disclosed suturing device comprises two rotatable wheels, wherein the first and second rotatable wheels are arranged to rotate in the same direction, and wherein outer profiles of the wheels are shifted in relation to each other when the wheel rotates.

The rotatable wheels may comprise a number of cam element distributed along an outer profile or contour of the each wheel. The distance from the center of the wheel to the outer periphery of the wheel can be said to determine the position of the corresponding wheel engagement element. Hence, when a wheel rotates the wheel engagement element moves back and forth in an axial direction of the jaw element.

This movement can be used in a mechanism to retain and release the double-ended needle. The cam elements may therefore be shaped such that when the rotation wheels rotate, the shape of the cam elements control the movement backwards and forwards of the wheel engagement elements to retain and release the corresponding end of the double-ended needle.

Figure 4:
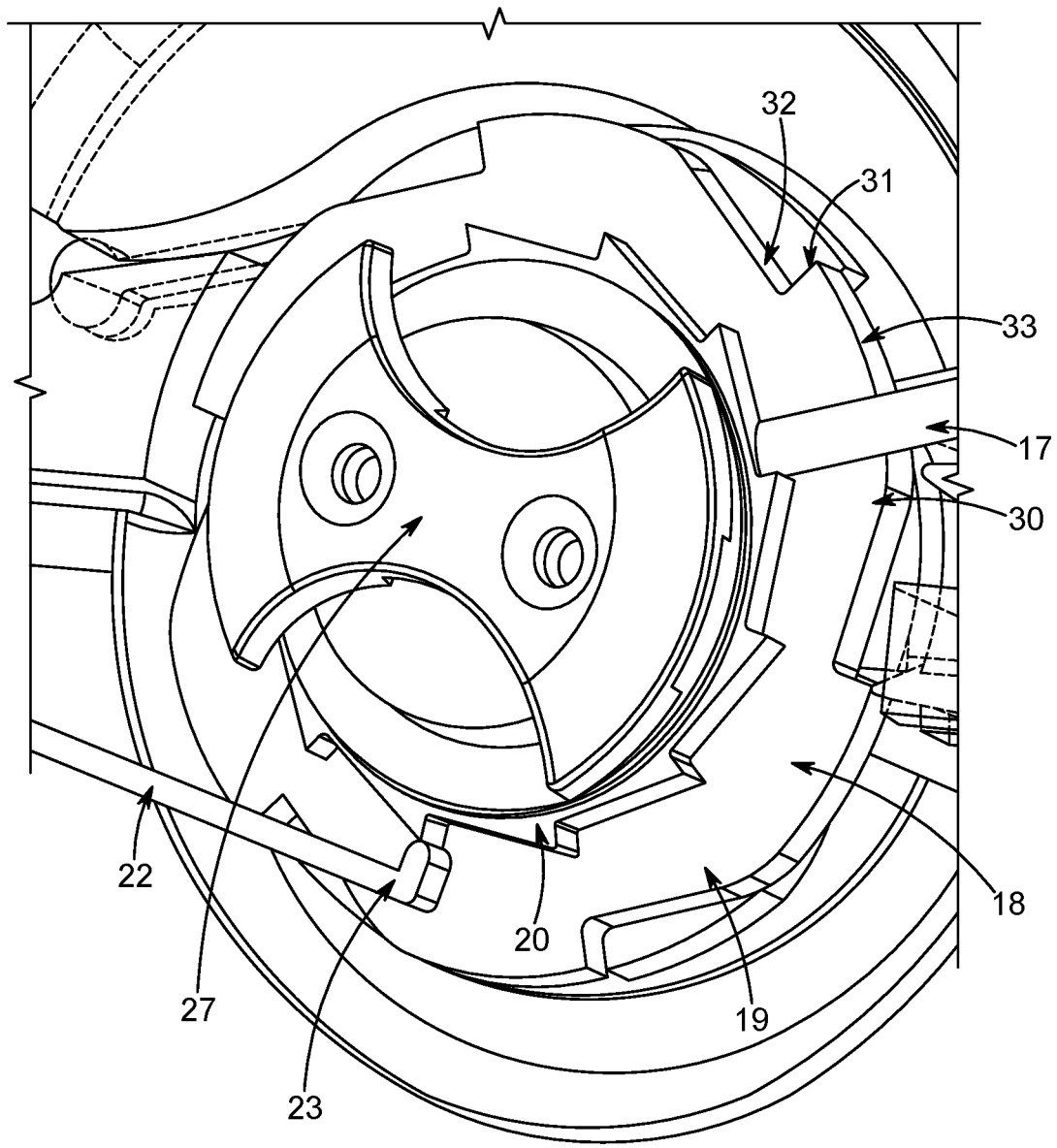
FIG. 4 is a detailed view showing an embodiment of one of the rotatable wheels having an inner portion and an outer portion, wherein at least the inner portion has an outer profile having cam elements and engaging with the needle lock device to control the position of the needle lock elements.

Each cam element may have a front ridge and a back ridge. The back ridge may be steeper than the front ridge. The rotational direction of the wheels are defined in relation to the shape of the wheel and exemplified in FIG. 4. In the configuration of the figure, the second rotation wheel will rotate clockwise, such that the second wheel engagement element will be in contact and first move along the longer front ridge (30) of the cam element and then fall into over the back ridge (31). The latter may correspond to a locking mechanism. In one embodiment, a border section (32) between the front ridge and the back ridge, which may also be seen as a groove or recess, is configured to hold the wheel engagement element of one of the needle lock devices in a retracted position causing the needle lock device to be in a locked configuration. An elevated section of each rotation wheel may be configured to hold the wheel engagement element of one of the needle lock devices in an extended position causing the needle lock device to be in a release configuration. FIG. 4 shows the second rotation wheel. The first rotation wheel may be mirrored in relation to the second rotation wheel. Hence, from an opposite perspective, i.e. viewing the suturing device form the opposite, the first rotation wheel may have the same shape as the second rotation wheel and may rotate clockwise from that perspective. Thus, the first and second rotation wheels may rotate in opposite directions.

The rotatable wheels may have separate portions for being driven to rotate and for controlling the needle lock devices. This may be implemented in the form of an inner portion and an outer portion, wherein the inner and outer portions are rigidly connected. The inner portion of the first rotatable wheel may be referred to as the first wheel inner portion. The inner portion of the second rotatable wheel may be referred to as the second wheel inner portion. The outer portion of the first rotatable wheel may be referred to as the first wheel outer portion. The outer portion of the second rotatable wheel may be referred to as the second wheel outer portion. The inner portion and the outer portion may have separate cam elements. An example of such an arrangement is shown in FIG. 4. The outer portion of each rotation wheel may engage with the wheel drive mechanisms of one of the jaw elements. The shape of the outer portion may therefore be adapted for this purpose, as can be seen in the example of FIG. 4. The inner portion of the rotation wheel may engage with the wheel engagement element of the same jaw element. The inner and outer portions do not necessarily have these configurations in the sense that the inner portion may, alternatively, be driven to rotate the wheel and the outer portion for controlling the needle lock devices.

The suturing device may further comprise reverse lock mechanisms to prevent the wheels from rotation backwards when the jaw elements are moved from a closed to an open position. A first reverse lock mechanism may be arranged to prevent the first rotatable wheel to rotate backwards when the first and second jaw elements are moved from the closed position to the open position. A second reverse lock mechanism may be arranged to prevent the second rotatable wheel to rotate backwards when the first and second jaw elements are moved from the closed position to the open position. The reverse lock mechanism may be implemented in the form of hook elements (23), as shown in FIG. 4, which can be hooked around an edge or ridge of the rotation wheels, such as hooked around an edge of the outer portion of the wheel, as shown in the example.

Wheel Driving Arrangements

Several embodiments for driving the rotation of the rotation wheels are possible.

In one embodiment, such as a one-handed embodiment, the user may hold the jaw elements in one hand and push the jaw elements together. In such an embodiment the jaw elements may comprise elements which engage with the rotation wheel and transfer a force to the wheels when the suturing device is being closed such that the wheels rotate. The suturing device may comprise a first wheel drive mechanism for rotation of the second rotation wheel and a second wheel drive mechanism for rotation of the first rotation wheel. The first wheel drive mechanism may be a first wheel drive shaft and the second wheel drive mechanism may be a second wheel drive shaft. The first wheel drive mechanism may be configured to propagate a force from the first jaw element to the second rotation wheel such that the second rotation wheel rotates in a first direction (forward) when the first and second jaws are moved from the open position to the closed position. The second wheel drive mechanism may operate in the same way. In one embodiment the presently disclosed suturing device comprises a jaw opening control element, which allows the user the manually control the rotatable wheels. There may also be two jaw opening control elements, one for each rotatable wheel, in order to be able to control the wheels individually. The jaw opening control element may be implemented, for example, as an extension of the rotatable wheels. The rotatable wheels may thereby have a first mechanical portion that is typically not directly exposed to the user. This portion may comprise the inner and outer portions of the rotatable wheel. This mechanical parts are typically placed behind a casing of the suturing device. The jaw opening control element may be an exposed part of the rotatable wheel, preferably comprising a grip or handle. The user can then control the locking and releasing of the needle manually by applying a force to the jaw opening control element.

Figure 7:
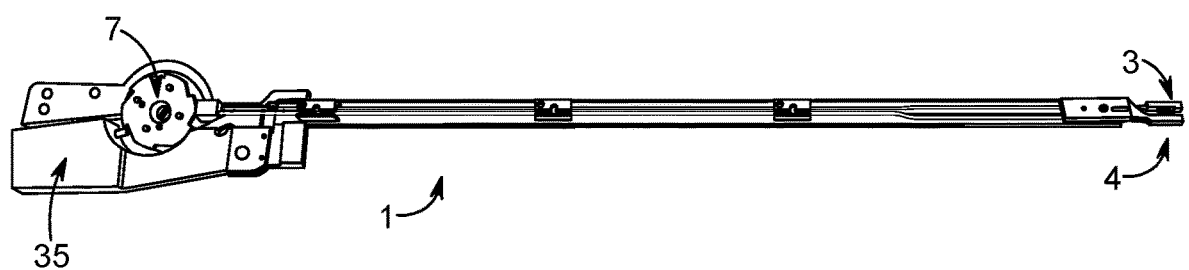
FIG. 7 is a perspective view of another embodiment of the presently disclosed suturing device with built-in needle-transfer of a double-ended needle, wherein the two rotatable wheels are arranged to rotate in the same direction and outer profiles of the wheels are shifted in relation to each other.
Figure 8:
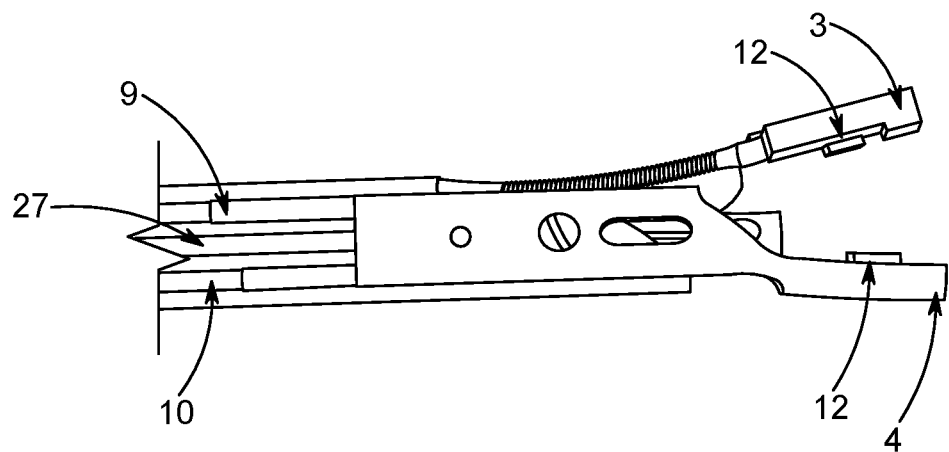
FIG. 8 is a detailed view an embodiment of two jaw elements with two wheel engagement elements.

In a second embodiment the wheels may be driven by a multidrive element (35), for example a handle, as shown in the example of FIG. 7. The handle may drive both the rotation wheels and the opening/closing of the jaw elements. As long as these two mechanisms are synchronized such that the closing of the jaw elements correspond to a sequence of mechanism for retaining and releasing the double-ended needle, several embodiments are possible. In the example of FIG. 7, there are three control elements extending along the device, as also shown in FIG. 8. A jaw opening control element (27) in the form of a shaft (27) controls the opening and closing of the jaw elements (3, 4), preferably assisted by a spring. The needle retention elements (12) are controlled by two wheel engagement elements (9, 10) in the form of two further shafts (9, 10). The mechanisms are preferably synchronized in the sense that the handle controls them.

DETAILED DESCRIPTION OF DRAWINGS

The invention will in the following be described in greater detail with reference to the accompanying drawings. The drawings are exemplary and are intended to illustrate some of the features of the presently disclosed suturing device, and are not to be construed as limiting to the presently disclosed invention.

FIG. 1 shows one embodiment of the presently disclosed suturing device (1) with built-in needle-transfer of a double-ended needle (2), wherein two rotatable wheels (7, 8) are arranged to rotate in opposite directions to control the retention and release of two needle lock devices (5,6). Two jaw elements (3, 4) are pivotable in relation to each other around a common pivot joint (24). A jaw opening spring (25) moves the jaws back to an open position after a user has pushed the jaw elements (3, 4) together to transfer the double-ended needle (2). The first jaw element (3) has a first needle lock device (5). The second jaw element (4) has a second needle lock device (6). A first rotatable wheel (7) has a first wheel inner portion (19) and a first wheel outer portion (not visible). A second rotatable wheel (8) has a second wheel inner portion (19') and a second wheel outer portion (20'). A first wheel engagement element (9), which is part of the first needle lock device (5), engages with an outer contour of the inner portion (19) of the first rotatable wheel (7). A second wheel engagement element (10), which is part of the second needle lock device (6), engages with an outer contour of the inner portion (19') of the second rotatable wheel (8). First springs (11) maintain a pressure from the wheel engagement elements (9, 10) to the corresponding rotatable wheel (7, 8). The needle lock devices (5, 6) each comprise a needle retention element (12) and a needle pusher element (13) configured to push the double-ended needle (2) backwards (i.e. towards the wheels). Each needle lock device (5, 6) comprises a needle pusher connecting element (15) and a second spring (14) for maintaining a pressure on the needle pusher element (13). Each needle lock device (5,6) comprises a needle pusher grip element (26) for limiting the axial movement between the needle pusher connecting element (15) and corresponding wheel engagement element (9, 10). A force from a first wheel drive mechanism (16) from the first jaw element (3) makes the second rotatable wheel (8) rotate. A force from a second wheel drive mechanism (17) from the second jaw element (4) makes the first rotatable wheel (7) rotate. Each rotatable wheel (7, 8) has a number of cam elements (18) distributed over the circumference. The suturing device (1) of the example comprises first and second reverse lock mechanisms (21, 22), each having a hook (23). A jaw opening control element (27) is rigidly connected to the one of the rotatable wheels. The jaw opening control element is arranged for manually controlling one of the first and second rotatable wheels to open the jaws (3, 4). A further jaw opening control element may be connected to the other of the rotatable wheels.

Figure 2:
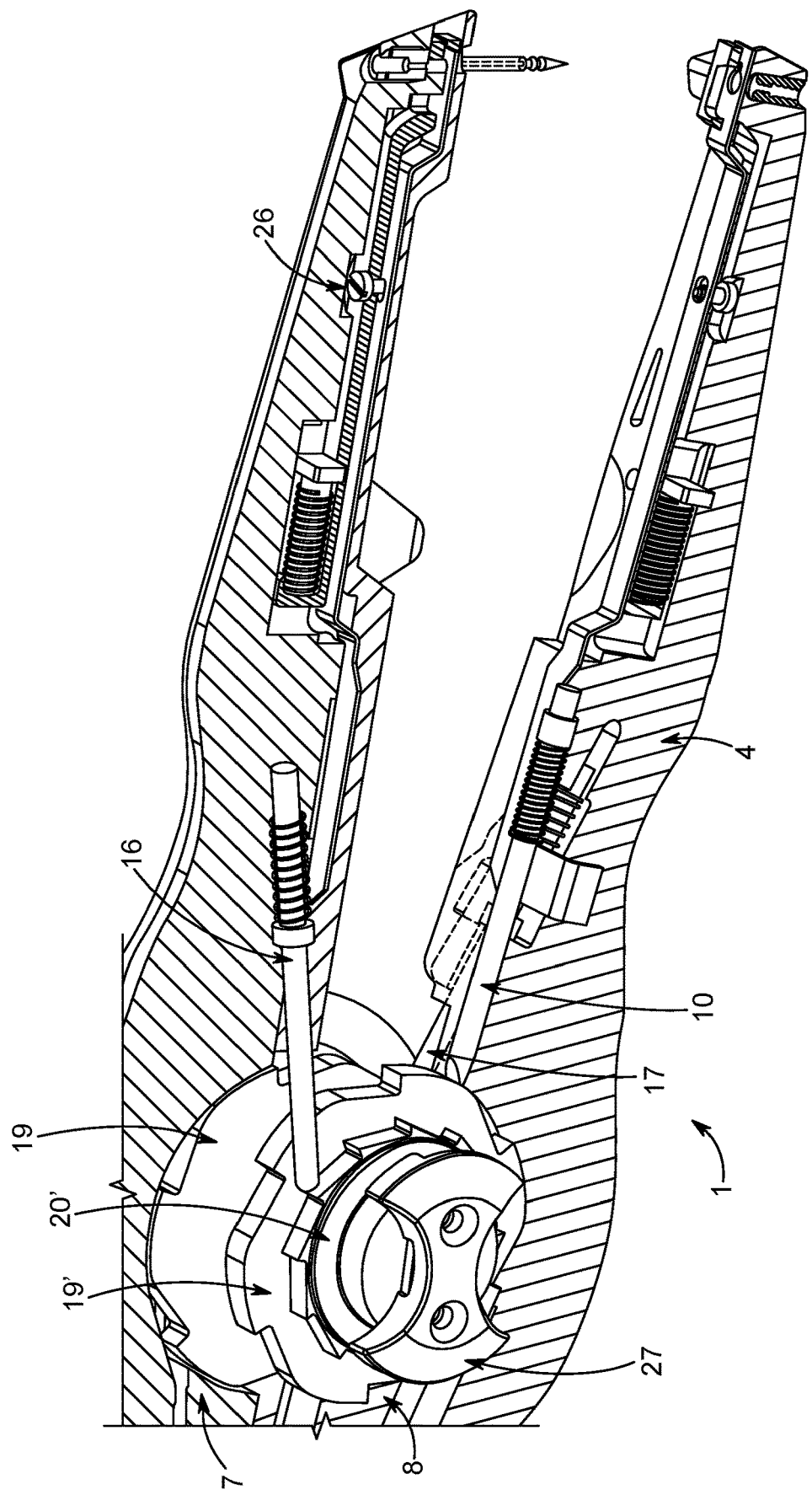
FIG. 2 is a perspective view of the suturing device of FIG. 1.

FIG. 2 shows a perspective view of the suturing device (1) of FIG. 1. From the perspective view it can be seen that the second rotatable wheel (8) has an inner portion (19') and an outer portion (20'). The inner portion (19') has a cam profile which can be used to move the wheel engagement element (10) of the second jaw element (4) backwards and forwards in the axial direction of the jaw element. The first wheel drive mechanism (16) is arranged to push the outer and smaller portion (20') to make the wheel rotate. The perspective also needle pusher grip element (26) in the form of a screw (26) arranged in a hole slightly wider than the screw (26). A jaw opening control element (27) is rigidly connected to the one of the rotatable wheels and arranged for manually controlling the second rotatable wheel (8) to control the jaws and/or the locking and releasing of the needle. A further jaw opening control element may be connected to the other of the rotatable wheels.

Figure 3:
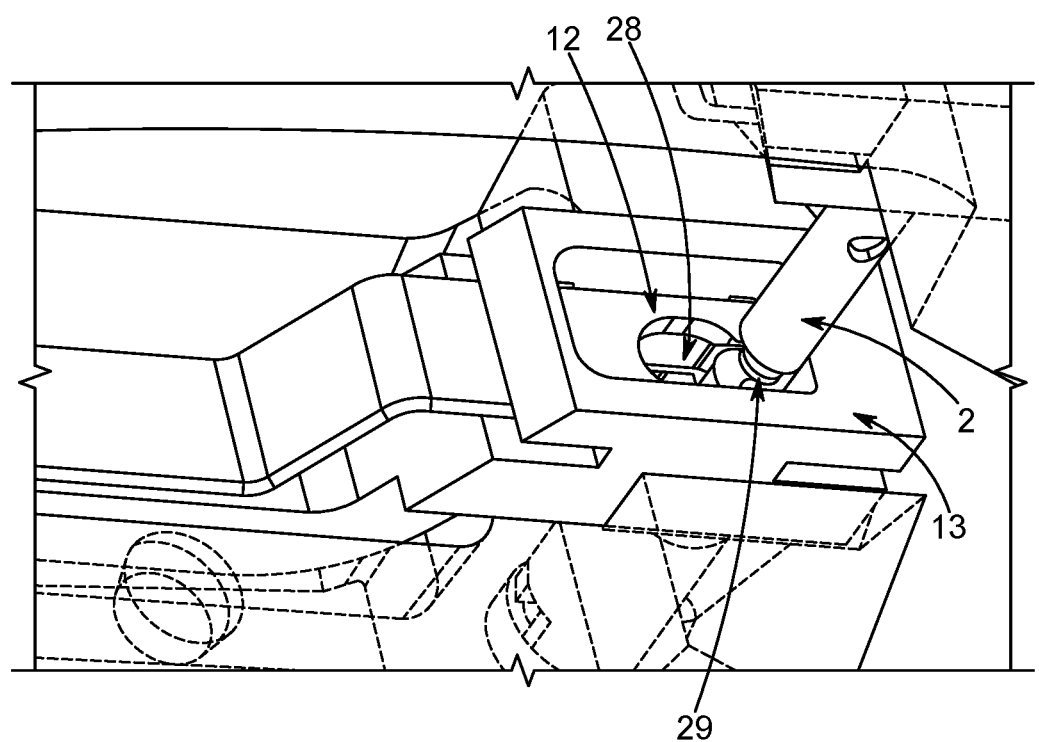
FIG. 3 is a detailed view showing an embodiment of the retention and release of one end of a needle.

FIG. 3 shows an embodiment of the retention and release of one end of a double-ended needle (2). A needle retention element (12) has a wider part (28) and a narrower part (29). If a narrower part of the needle (2) or a groove in the needle (2) is arranged in the narrow part (29), the needle (2) is in a locked position. The figure also discloses a needle pusher element (13) pushing the needle (2) backwards.

FIG. 4 shows an embodiment of one of the rotatable wheels having an inner portion (19) and an outer portion (20), wherein at least the inner portion (19) has an outer profile having a number of cam elements (18) and engaging with the needle lock device to control the position of the needle lock elements. Each cam element (18) of the inner portion (19) comprises a steep back ridge (31) and a curved front ridge (30). The border section (32) between the front ridge (30) and back ridge (31) corresponds to the second wheel engagement element (10) being in its leftmost position in the figure, corresponding to the needle lock device (6) being in a retention position. On the front ridge (30), which is the longer curved surface between two back ridges (31), there is an elevated section (33). When the second wheel engagement element (10) is placed on the elevated section (33), the needle lock device (6) is in a release configuration. A jaw opening control element (27) is rigidly connected to the outer portion (20) of the rotatable wheel. A further jaw opening control element may be connected to the other of the rotatable wheels.

Figure 5A:
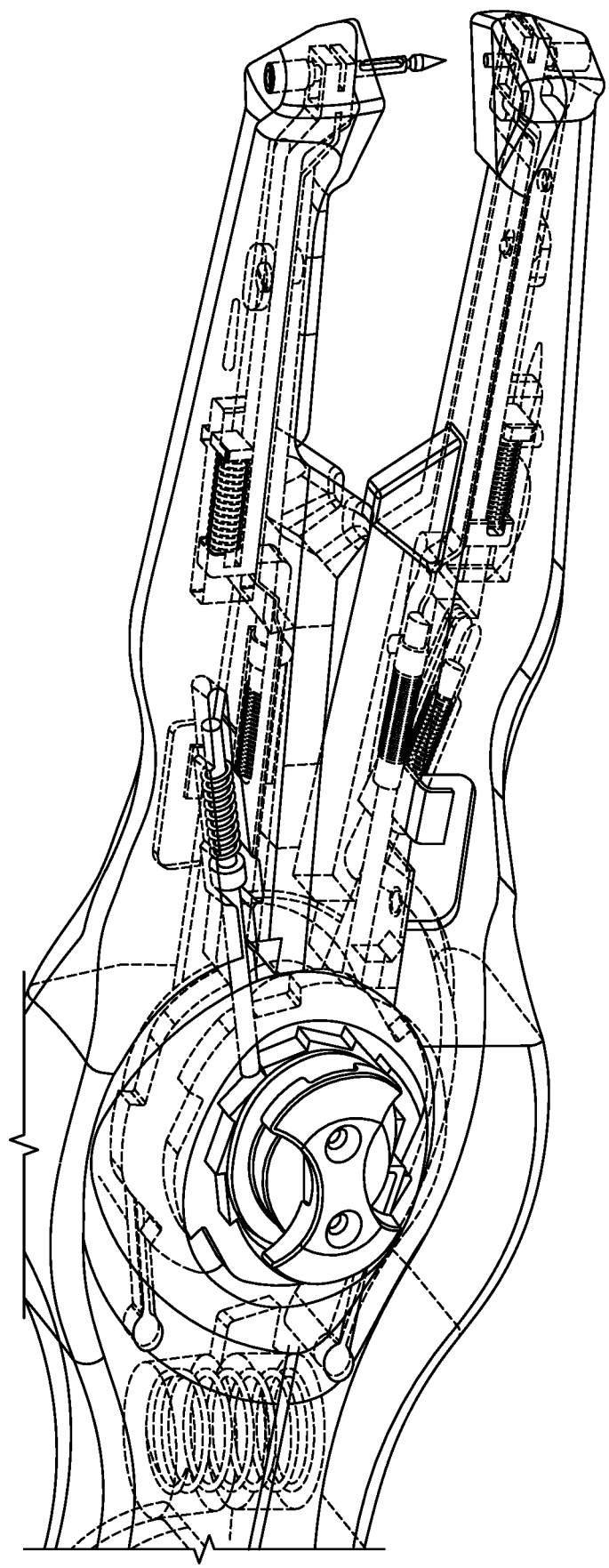
FIG. 5A-H are views showing an example of a sequence of steps of a closing procedure of the jaws, wherein each step corresponds to an angle between the jaw elements, explaining the sequence of mechanism for transferring the double-ended needle from one jaw to the other.
Figure 5B:
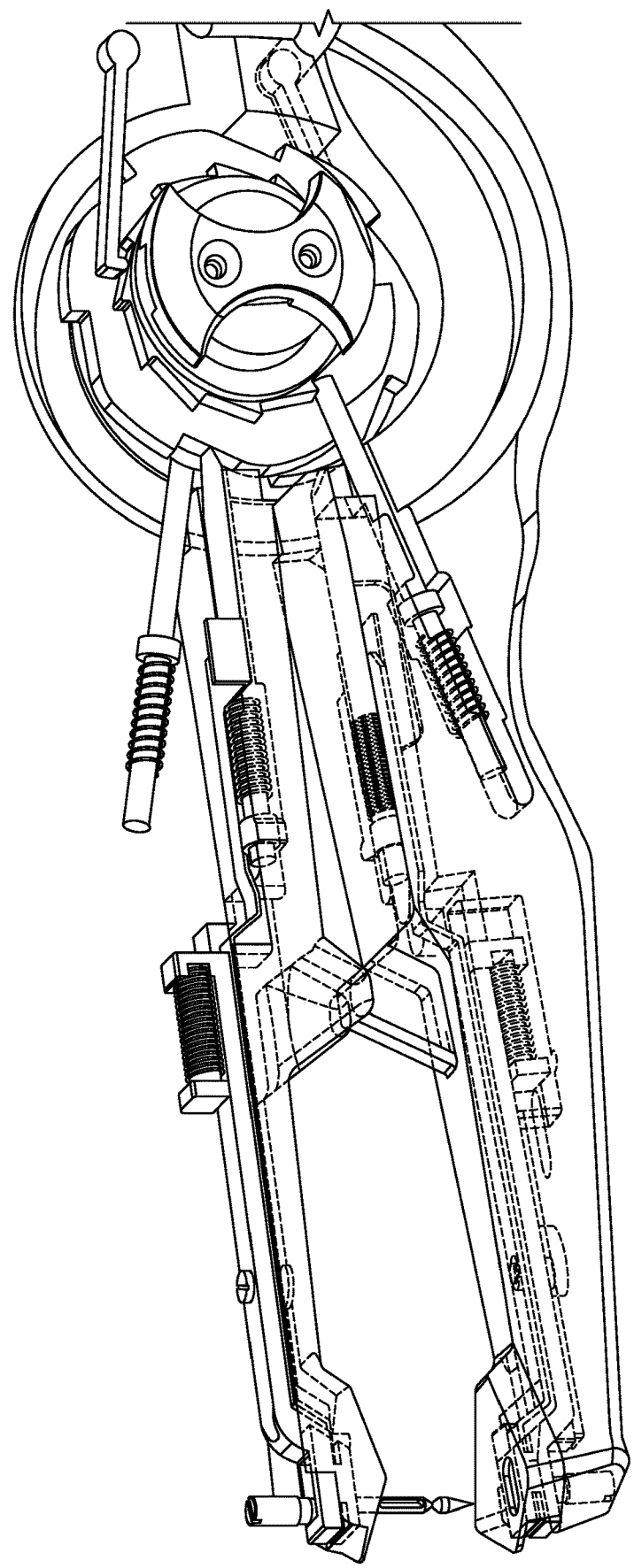
Figure 5C:
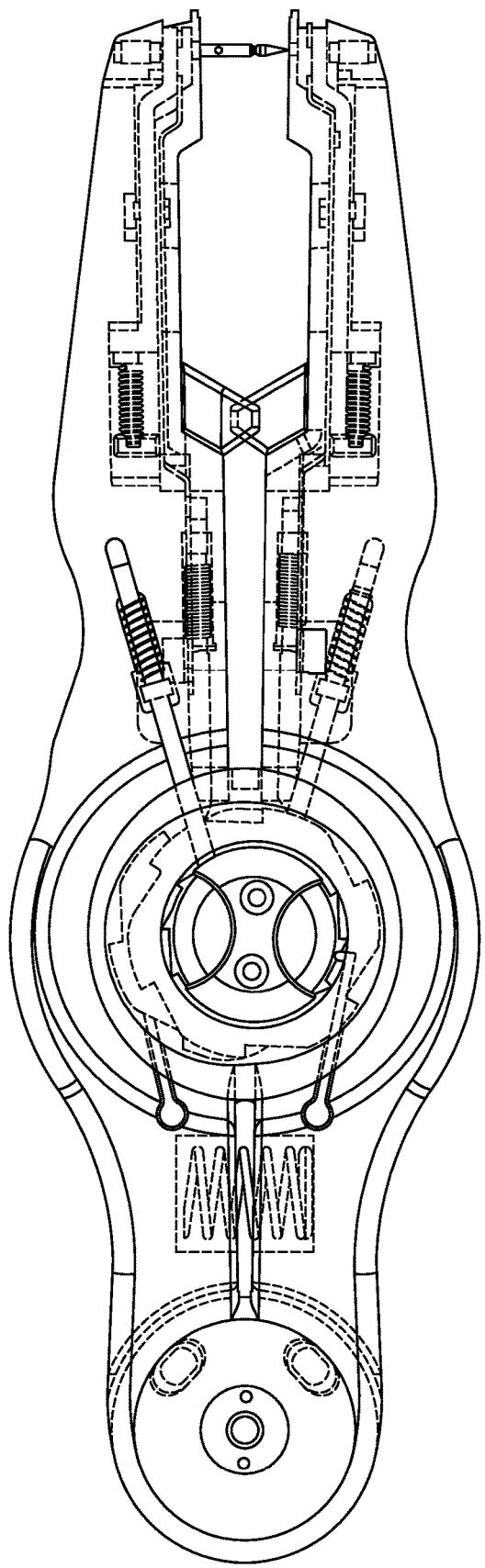
Figure 5D:
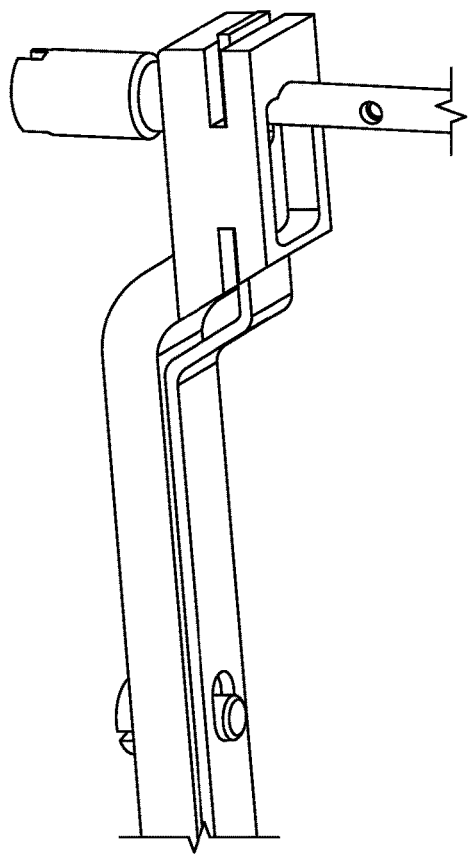
Figure 5E:
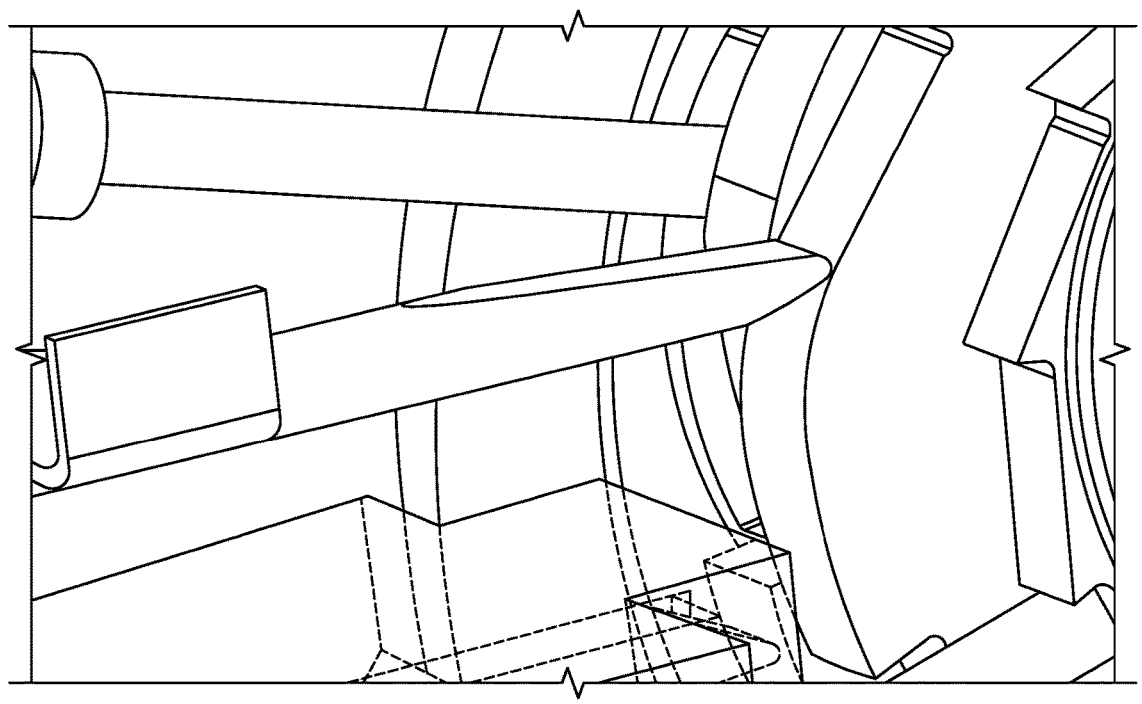
Figure 5F:
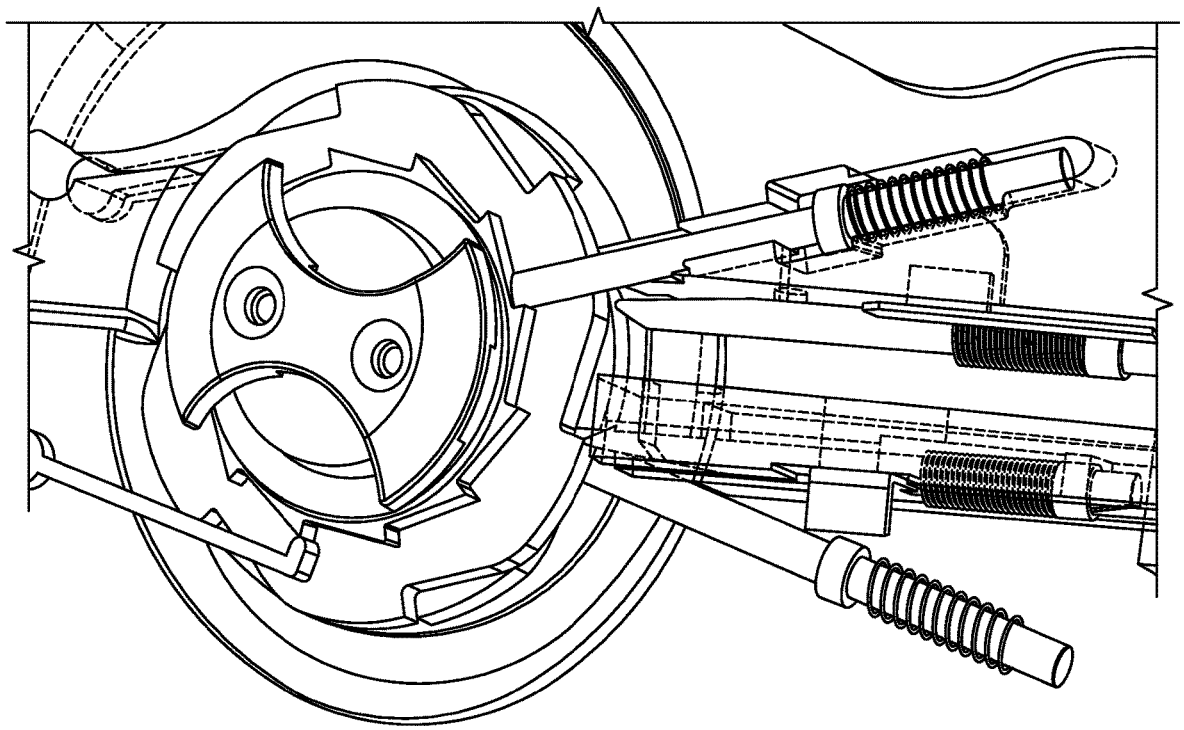
Figure 5G:
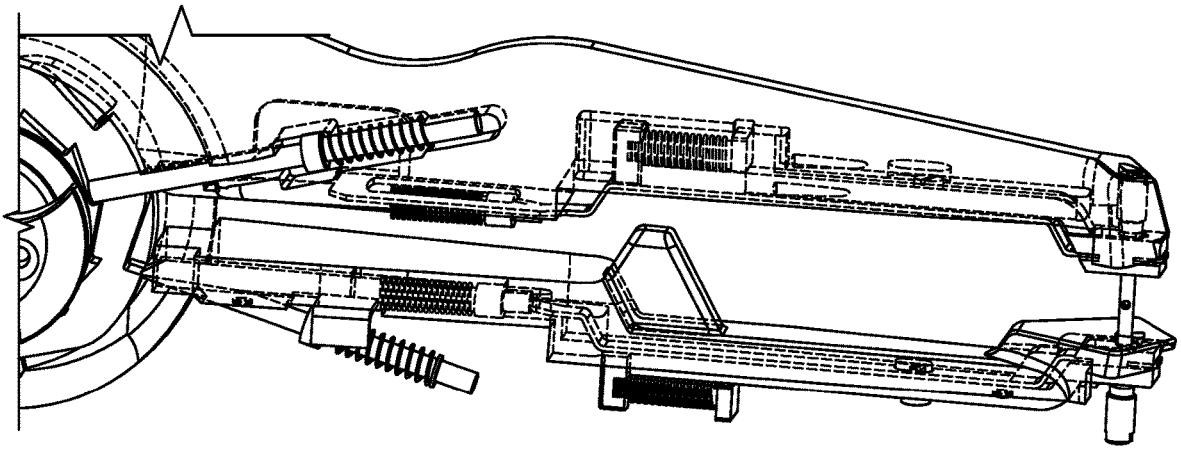
Figure 5H:
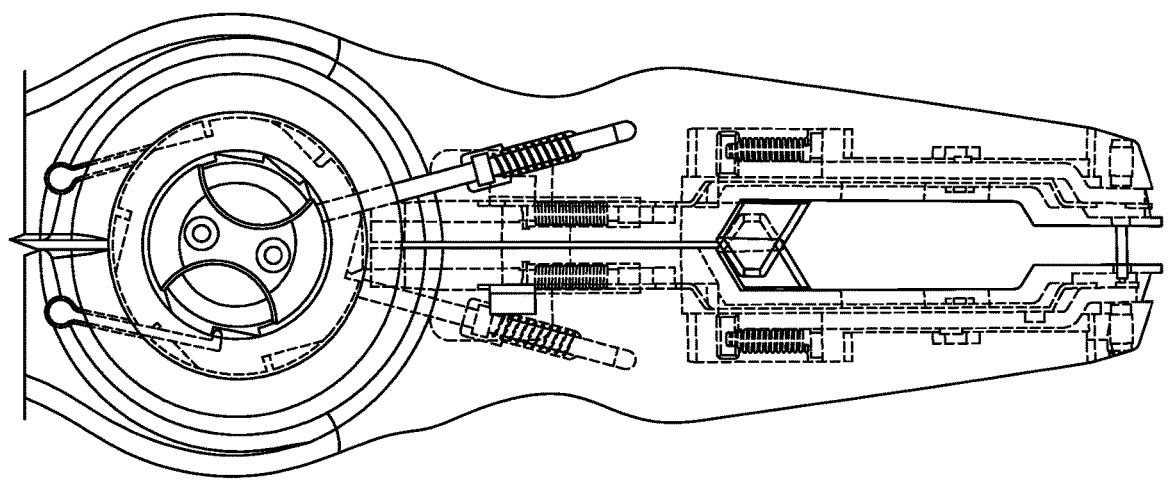

FIG. 5A-H show an example of sequence of steps of a closing procedure of the jaws, wherein each step corresponds to an angle between the jaw elements, explaining the sequence of mechanism for transferring the double-ended needle from one jaw to the other. FIG. 5A: At 2.3° between the jaw elements, second wheel drive mechanism (17) starts engaging with the outer portion (20). The same occurs at the first rotatable wheel. FIG. 5B, 1.53°: wheel drive mechanisms (16, 17) now drive the rotatable wheels in opposite directions. The first wheel engagement element (9) starts moving towards the double-ended needle (2), thereby starting the opening process of the first needle lock device (5). FIG. 5C, 1.1°: The double-ended needle (2) enters the needle retention element of the second jaw element. FIG. 5D, 1.0°, shows the first needle retention element (12) which is about to lose its grip of the double-ended needle (2). FIG. 5E, at 0.7°, shows the first wheel engagement element (9) and the inner portion (19) of the first rotatable wheel (7). The first wheel engagement element (9) is about to enter a curved section of the cam element. In this position the needle is loose from the needle retention element (12) of the first needle lock device (5). FIG. 5F: at 0.2° the second wheel engagement element (10) is about to go down the back ridge (31) of a cam element (18) of the second rotatable wheel (8). FIG. 5G, 0.12°: the second wheel engagement element (10) is passing the back ridge (31) and thereby locks the double-ended needle (2) in the retention element (12) of the second needle lock device (6). FIG. 5H, 0°: In this position the double-ended needle (2) is locked in the retention element (12) of the second needle lock device (6).

FIG. 6 shows an embodiment of the needle retention element (12) with an opening for receiving and locking the needle (2), the opening having a wide section (28) and a narrow section (29). The needle retention element (12) is configured in locked position. A needle pusher element (13) is arranged to push the needle (2) backwards against a body part (36) of the jaw element.

FIG. 7 shows another embodiment of the presently disclosed suturing device (6) with built-in needle-transfer of a double-ended needle (2), wherein the two rotatable wheels (7, 8) are arranged to rotate in the same direction and outer profiles of the wheels are shifted in relation to each other. This embodiment comprises a multidrive element (35) for driving both the opening/closing of the jaw elements (3, 4) and the two rotatable wheels (7, 8). This mechanism is further described in FIGS. 7-8.

FIG. 8 shows an embodiment of two jaw elements (3, 4) with two wheel engagement elements (9, 10). A jaw opening control element (27) in the form of a shaft (27) controls the opening and closing of the jaw elements (3, 4), preferably assisted by a spring. The needle retention elements (12) are controlled by two wheel engagement elements (9, 10) in the form of two further shafts (9, 10). The first engagement element (9) controls the retention and release of the first jaw element (3). The second engagement element (10) controls the retention and release of the second jaw element (4). If the outer profiles of the wheels are shifted in relation to each other when the wheel rotates, the shafts move backward and forwards in the axial direction of the device to control the retention and release of the double-ended needle.

Figure 9:
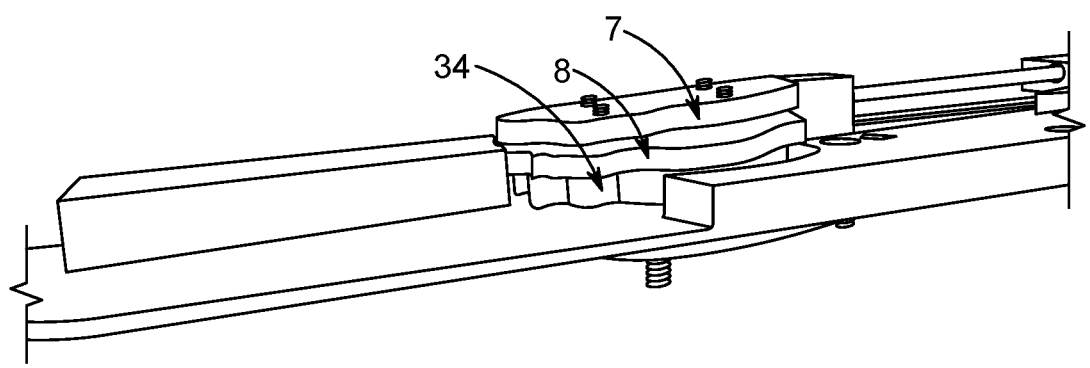
FIG. 9 is a detailed view showing two rotatable wheels arranged to rotate in the same direction wherein the outer profiles are shifted in relation to each other, and a common drive wheel connected to the two rotational wheel.

FIG. 9 shows two rotatable wheels (7, 8) arranged to rotate in the same direction wherein the outer profiles are shifted in relation to each other, and a common drive wheel (34) connected to the two rotational wheels (7, 8).

LIST OF ELEMENTS IN FIGURES

1—suturing device
2—double-ended needle

3—first jaw element
4—second jaw element
5—first needle lock device
6—second needle lock device
7—first rotatable wheel
8—second rotatable wheel
9—first wheel engagement element
10—second wheel engagement element
11—first spring
12—needle retention element
13—needle pusher element
14—second spring
15—needle pusher connecting element
16—first wheel drive mechanism
17—second wheel drive mechanism
18—cam element
19—inner portion
20—outer portion
21—first reverse lock mechanism
22—second reverse lock mechanism
23—hook
24—pivot joint
25—jaw opening spring
26—needle pusher grip element
27—jaw opening control element
28—wide section (of needle retention element)
29—narrow section (of needle retention element)
30—front ridge (of cam element)
31—back ridge (of cam element)
32—border section between the front ridge and the back ridge
33—elevated section (of cam element)
34—common drive wheel
35—multidrive element
36—body part (of the jaw element)

Further Details of the Invention

1. A suturing device with a needle-transfer of a double-ended needle, the suturing device comprising:
   a first jaw element comprising a first needle lock device for retaining and releasing a first end of the double-ended needle;
   a second jaw element comprising a second needle lock device for retaining and releasing a second end of the double-ended needle,
   wherein the first and second jaw elements are movable in relation to each other between an open position and a closed position;
   a needle-transferring mechanism for alternately transferring the double-ended needle from one of the jaw elements to the other when the first and second jaws are moved from the open position to the closed position, said needle-transferring mechanism comprising:
      a first rotatable wheel connected to the first needle lock device; and
      a second rotatable wheel connected to the second needle lock device, wherein the first and second rotatable wheels are arranged such that a rotation of the first and second rotatable wheels causes one of the needle lock devices to lock the double-ended needle and the other needle lock device to release the double-ended needle when the first and second jaw elements are moved in relation to each other from the open position to the closed position.
2. The suturing device according to item 1, wherein the first rotatable wheel comprises a first wheel inner portion rigidly connected to a first wheel outer portion, and wherein the second rotatable wheel comprises an second wheel inner portion rigidly connected to a second wheel outer portion.
3. The suturing device according to item 2, wherein a first force is propagated from the first jaw element to the second rotatable wheel and wherein a second force is propagated from the second jaw element to the first rotatable wheel when the first and second jaw elements are moved in relation to each other from the open position to the closed position, thereby causing the first and second rotatable wheels to rotate
4. The suturing device according to any of the preceding items, wherein the first and second rotatable wheels are arranged to rotate in opposite directions when the first and second jaw elements are moved in relation to each other from the open position to the closed position, thereby causing one of the needle lock devices to lock the double-ended needle and the other needle lock device to release the double-ended needle.
5. The suturing device according to item 1, wherein the first and second rotatable wheels are arranged to rotate in the same direction, wherein outer profiles of the wheels are shifted in relation to each other when the wheel rotates.
6. The suturing device according to any of the preceding items, wherein the first and second rotatable wheels are arranged to rotate simultaneously and/or synchronized, preferably with the same rotational speed.
7. The suturing device according to any of the preceding items, wherein each needle lock device comprises a wheel engagement element engaging with the first and second rotatable wheels, respectively.
8. The suturing device according to item 7, wherein each wheel engagement element is configured to move backwards and forwards in the axial direction of the corresponding jaw element in response to a rotation of the corresponding rotatable wheel.
9. The suturing device according to item 8, wherein a movement backwards and forwards of each wheel engagement element causes the corresponding needle lock device to retain and release the corresponding end of the double-ended needle, respectively.
10. The suturing device according to item 9, wherein each wheel engagement element is an engagement shaft.
11. The suturing device according to any of items 2-10, wherein each wheel engagement element comprises a first spring configured to maintain a pressure from the wheel engagement element to the corresponding rotatable wheel.
12. The suturing device according to any of items 2-11, wherein each wheel engagement element is connected to a needle retention element, the needle retention element extending in the longitudinal direction of the corresponding jaw element.
13. The suturing device according to item 12, wherein each needle retention element comprises an opening for receiving the double-ended needle, wherein the opening has a shape capable of locking the double-ended needle.
14. The suturing device according to item 13, wherein the opening has a wide section and narrow section, wherein a narrow portion of the double-ended needle can be locked in the narrow section.
15. The suturing device according to any of the preceding items, wherein each needle lock device comprises a needle pusher element configured to push the double-ended needle backwards towards a body part of the corresponding jaw element.

16. The suturing device according to item 15, wherein each needle lock device further comprises a needle pusher connecting element and a second spring configured to maintain a pressure on the needle pusher element towards the body part.

17. The suturing device according to any of the preceding items, further comprising a first wheel drive mechanism for rotation of the first rotation wheel and a second wheel drive mechanism for rotation of the second rotation wheel.

18. The suturing device according to item 17, wherein first wheel drive mechanism is a first wheel drive shaft and the second wheel drive mechanism is a second wheel drive shaft.

19. The suturing device according to any of items 17-18, wherein the first wheel drive mechanism is configured to propagate a force from the first jaw element to the second rotation wheel such that the second rotation wheel rotates in a first direction when the first and second jaws are moved from the open position to the closed position.

20. The suturing device according to item 19, wherein the second wheel drive mechanism is configured to propagate a force from the second jaw element to the first rotation wheel such that the first rotation wheel rotates in a second direction opposite to the first direction when the first and second jaws are moved from the open position to the closed position.

21. The suturing device according to any of the preceding items, wherein each of the rotation wheels have cam elements.

22. The suturing device according to item 21, wherein the cam elements are shaped such that when the rotation wheels rotate, the shape of the cam elements control the movement backwards and forwards of the wheel engagement elements to retain and release the corresponding end of the double-ended needle.

23. The suturing device according to any of items 21-22, wherein each cam element has a front ridge and a back ridge, wherein the back ridge is steeper than the front ridge.

24. The suturing device according to item 23, wherein a border section between the front ridge and the back ridge is configured to hold the wheel engagement element of one of the needle lock devices in a retracted position causing the needle lock device to be in a locked configuration.

25. The suturing device according to any of items 23-24, wherein an elevated section of each rotation wheel is configured to hold the wheel engagement element of one of the needle lock devices in an extended position causing the needle lock device to be in a release configuration.

26. The suturing device according to any of the preceding items, wherein each of the rotatable wheels comprises in inner portion and an outer portion, wherein the inner and outer portions are rigidly connected.

27. The suturing device according to item 26, wherein the inner portion and the outer portion have separate cam elements.

28. The suturing device according to any of items 26-27, wherein the outer portion of each rotation wheel engages with the wheel drive mechanisms of one of the jaw elements and the inner portion of each rotation wheel engages with the wheel engagement element of the same jaw element.

29. The suturing device according to any of the preceding items, further comprising a first reverse lock mechanism configured to prevent the first rotatable wheel to rotate backwards when the first and second jaw elements are moved from the closed position to the open position, and a second reverse lock mechanism configured to prevent the second rotatable wheel to rotate backwards when the first and second jaw elements are moved from the closed position to the open position.

30. The suturing device according to any of the preceding items, further comprising a jaw opening control element for manually controlling the first and/or second rotatable wheels to open the jaws.

31. The suturing device according to any of the preceding items, wherein the needle-transferring mechanism is automatic.

32. The suturing device according to any of the preceding items, wherein the jaw elements are pivotable in relation to each other around a common pivot joint.

33. The suturing device according to any of the preceding items, further comprising a jaw opening spring arranged between the first jaw element and the second jaw element.

34. The suturing device according to any of the preceding items, wherein the suturing device is disposable.

The invention claimed is:

1. A suturing device with a needle-transfer of a double-ended needle, the suturing device comprising:
   a first jaw element comprising a first needle lock device for retaining and releasing a first end of the double-ended needle;
   a second jaw element comprising a second needle lock device for retaining and releasing a second end of the double-ended needle,
   wherein the first and second jaw elements are movable in relation to each other between an open position and a closed position;
   a needle-transferring mechanism for alternately transferring the double-ended needle from one of the first and second jaw elements to the other when the first and second jaw elements are moved from the open position to the closed position, said needle-transferring mechanism comprising:
   a first rotatable wheel connected to the first needle lock device, said first rotatable wheel comprising a first wheel inner portion rigidly connected to a first wheel outer portion, wherein the first wheel inner portion and the first wheel outer portion have separate cam element profiles; and
   a second rotatable wheel connected to the second needle lock device, said second rotatable wheel comprising a second wheel inner portion rigidly connected to a second wheel outer portion, wherein the second wheel inner portion and the second wheel outer portion have separate cam element profiles,
   wherein a first force is propagated from the first jaw element to the second rotatable wheel and wherein a second force is propagated from the second jaw element to the first rotatable wheel when the first and second jaw elements are moved in relation to each other from the open position to the closed position, thereby causing the first and second rotatable wheels to rotate, wherein the first and second rotatable wheels are arranged such that a rotation of the first and second rotatable wheels causes one of the first and second needle lock devices to lock the double-ended needle and the other of the first and second needle lock devices to release the double-ended needle.

2. The suturing device according to claim 1, wherein the first and second rotatable wheels are arranged to rotate in opposite directions when the first and second jaw elements are moved in relation to each other from the open position to the closed position, thereby causing one of the first and second needle lock devices to lock the double-ended needle and the other of the first and second needle lock devices to release the double-ended needle.

3. The suturing device according to claim 1, wherein the first and second rotatable wheels are arranged to rotate in the same direction, wherein outer profiles of the first and second rotatable wheels are shifted in relation to each other when the first and second rotatable wheels rotate.

4. The suturing device according to claim 1, further comprising a first wheel drive mechanism engaging with the second wheel outer portion.

5. The suturing device according to claim 1, further comprising a second wheel drive mechanism engaging with the first wheel outer portion.

6. The suturing device according to claim 1, wherein the first and second rotatable wheels are arranged to rotate simultaneously and/or synchronized, preferably with the same rotational speed.

7. The suturing device according to claim 1, wherein the first needle lock device comprises a first wheel engagement element engaging with the first rotatable wheel, and wherein the second needle lock device comprises a second wheel engagement element engaging with the second rotatable wheel.

8. The suturing device according to claim 7, wherein the first wheel engagement element engages with the first wheel inner portion.

9. The suturing device according to claim 7, wherein the second wheel engagement element engages with the second wheel inner portion.

10. The suturing device according to claim 7, wherein:
the first wheel engagement element is configured to move backwards and forwards in an axial direction of the first jaw element in response to the rotation of the first rotatable wheel and wherein a movement backwards and forwards of the first wheel engagement element causes the first needle lock device to retain and release the first end of the double-ended needle, respectively; and
the second wheel engagement element is configured to move backwards and forwards in an axial direction of the second jaw element in response to the rotation of the second rotatable wheel and wherein a movement backwards and forwards of the second wheel engagement element causes the second needle lock device to retain and release the second end of the double-ended needle, respectively.

11. The suturing device according to claim 7, wherein each of the first rotatable wheel and the second rotatable wheel have cam elements shaped such that when rotated, the shape of the cam elements controls the movement backwards and forwards of the first and second wheel engagement elements to retain and release corresponding respective ends of the double-ended needle.

12. The suturing device according to claim 11, wherein each cam element has a front ridge and a back ridge, wherein the back ridge is steeper than the front ridge.

13. The suturing device according to claim 12, wherein a border section between the front ridge and the back ridge is configured to hold the wheel engagement element of one of the first and second needle lock devices in a retracted position causing the one of the first and second needle lock devices to be in a locked configuration.

14. The suturing device according to claim 12, wherein:
an elevated section of the first rotatable wheel is configured to hold the first wheel engagement element of the first needle lock device in an extended position causing the first needle lock device to be in a release configuration; and
an elevated section of the second rotatable wheel is configured to hold the second wheel engagement element of the second needle lock device in an extended position causing the second needle lock device to be in a release configuration.

15. The suturing device according to claim 1, further comprising a jaw opening control element for manually controlling the first and/or second rotatable wheels to open the first and second jaw elements.

16. The suturing device according to claim 15, wherein the jaw opening control element is rigidly connected to one of the first rotatable wheel or the second rotatable wheel.

17. The suturing device according to claim 15, comprising a further jaw opening control element, wherein the jaw opening control element and further jaw opening control element are arranged to control the first and second rotatable wheels individually.

18. A suturing device with a needle-transfer of a double-ended needle, the suturing device comprising:
a first jaw element comprising a first needle lock device for retaining and releasing a first end of the double-ended needle;
a second jaw element comprising a second needle lock device for retaining and releasing a second end of the double-ended needle,
wherein the first and second jaw elements are movable in relation to each other between an open position and a closed position;
a needle-transferring mechanism for alternately transferring the double-ended needle from one of the first and second jaw elements to the other when the first and second jaw elements are moved from the open position to the closed position, said needle-transferring mechanism comprising:
a first rotatable wheel connected to the first needle lock device, said first rotatable wheel comprising a first rotation axis and a first wheel inner portion rigidly connected to a first wheel outer portion; and
a second rotatable wheel connected to the second needle lock device, said second rotatable wheel comprising a second rotation axis coaxially aligned with the first rotation axis and a second wheel inner portion rigidly connected to a second wheel outer portion,
wherein a first force is propagated from the first jaw element to the second rotatable wheel and wherein a second force is propagated from the second jaw element to the first rotatable wheel when the first and second jaw elements are moved in relation to each other from the open position to the closed position, thereby causing the first and second rotatable wheels to rotate, wherein the first and second rotatable wheels are arranged such that a rotation of the first and second rotatable wheels causes one of the first and second needle lock devices to lock the double-ended needle and the other of the first and second needle lock devices to release the double-ended needle.

19. The suturing device according to claim 18, wherein the first needle lock device comprises a first wheel engagement element engaging with the first rotatable wheel, and wherein the second needle lock device comprises a second wheel engagement element engaging with the second rotatable wheel.

20. The suturing device according to claim 19, wherein each of the first rotatable wheel and the second rotatable wheel have cam elements shaped such that when rotated, the shape of the cam elements controls the movement backwards and forwards of the first and second wheel engagement elements to retain and release corresponding respective ends of the double-ended needle.

* * * * *